(12) United States Patent
Matthews

(10) Patent No.: US 12,171,600 B2
(45) Date of Patent: *Dec. 24, 2024

(54) STERILE DRAPE WITH ELASTICIZED BODY PORTION FOR PROTECTING A C-arm IMAGING MACHINE

(71) Applicant: Medline Industries, LP, Northfield, IL (US)

(72) Inventor: Steffanie Thompson Matthews, Cumming, GA (US)

( * ) Notice: Subject to any disclaimer, the term of this patent is extended or adjusted under 35 U.S.C. 154(b) by 364 days.

This patent is subject to a terminal disclaimer.

(21) Appl. No.: 17/665,487

(22) Filed: Feb. 4, 2022

(65) Prior Publication Data

US 2022/0280127 A1 Sep. 8, 2022

Related U.S. Application Data

(63) Continuation of application No. 16/851,760, filed on Apr. 17, 2020, now Pat. No. 11,246,549.

(Continued)

(51) Int. Cl.
*A61B 6/00* (2024.01)
(52) U.S. Cl.
CPC .......... *A61B 6/4423* (2013.01); *A61B 6/4441* (2013.01)
(58) Field of Classification Search
CPC ..... A61B 6/4441; A61B 46/10; A61B 6/4423; A61B 46/40; A61B 6/4405; A61B 6/462; A61B 50/13; A61B 34/30; A61B 34/35; A61B 2034/302; A61B 2017/00991; A61B 2017/00477; A61B 50/30; A61B 46/13;

(Continued)

(56) References Cited

U.S. PATENT DOCUMENTS 2,491,894 A 12/1949 Fox
2,772,886 A 12/1956 Parmele
(Continued)

FOREIGN PATENT DOCUMENTS

CN 102112068 B 7/2013
CN 103356296 B 3/2016
(Continued)

OTHER PUBLICATIONS

C-Arm Drapes, Dasol International, Retrieved online from http://www.dasolin.com/carm_drape_eng.html on Jan. 16, 2019, 1 page.

(Continued)

*Primary Examiner* — Irakli Kiknadze
(74) *Attorney, Agent, or Firm* — Fredrickson & Byron, P.A.

(57) ABSTRACT

A sterile drape can be used to cover a C-arm imaging machine used during a medical procedure. In some configurations, the drape includes a detector body cover, a C-arm body cover, and an elastic banding. The detector body cover can be positioned around a detector of the imaging machine. The C-arm body cover can include a tunnel portion that is positioned to surround a portion of the C-arm extending away from the detector. The elastic banding can extend about a perimeter of a junction between the detector body cover and the C-arm body cover. The elastic banding can provide a biasing force that draws the junction between the detector body cover and the C-arm body cover closed.

16 Claims, 9 Drawing Sheets

Related U.S. Application Data

(60) Provisional application No. 62/836,455, filed on Apr. 19, 2019.

(58) Field of Classification Search
CPC ... A61B 2046/205; A61B 46/20; A61B 6/487; A61B 46/00; A61B 2090/3764; A61B 2017/00902; A61B 90/39; A61B 2090/3983; G21F 3/00; G21F 9/001
USPC .......................................................... 378/204
See application file for complete search history.

(56) References Cited

U.S. PATENT DOCUMENTS

| | | | |
|---|---|---|---|
| 3,625,205 | A | 12/1971 | Madden et al. |
| 3,698,791 | A | 10/1972 | Walchle et al. |
| 3,809,077 | A | 5/1974 | Hansen |
| 3,835,851 | A | 9/1974 | Mllari |
| 3,952,738 | A | 4/1976 | Krzewinski |
| 4,799,779 | A | 1/1989 | Mesmer |
| 5,379,703 | A | 1/1995 | Marshall |
| 5,426,683 | A | 6/1995 | O'Farrell, Jr. et al. |
| 5,490,524 | A | 2/1996 | Williams et al. |
| 5,506,882 | A | 4/1996 | O'Farrell, Jr. et al. |
| 5,583,909 | A | 12/1996 | Hanover |
| 5,802,719 | A | 9/1998 | O'Farrell, Jr. et al. |
| 6,478,061 | B2 | 11/2002 | Haberkorn |
| 7,040,484 | B1 | 5/2006 | Homra et al. |
| 7,044,132 | B2 | 5/2006 | Masini |
| 7,104,201 | B2 | 9/2006 | Comeaux et al. |
| 7,108,422 | B2 | 9/2006 | Borom |
| 7,305,991 | B2 | 12/2007 | Santilli et al. |
| 8,042,549 | B2 | 10/2011 | Kaska |
| 8,225,495 | B2 | 7/2012 | Dehler |
| 8,286,637 | B2 | 10/2012 | Kaska |
| 9,283,041 | B2 | 3/2016 | Adams |
| 9,295,521 | B2 | 3/2016 | Pack et al. |
| 9,307,945 | B2 | 4/2016 | Campista |
| 10,285,767 | B2 | 5/2019 | Marinchak |
| 11,246,549 | B2 * | 2/2022 | Matthews ............ A61B 6/4441 |
| 2005/0158510 | A1 | 7/2005 | Trump |
| 2005/0247722 | A1 | 11/2005 | Blocker |
| 2006/0161137 | A1 | 7/2006 | Orban, III et al. |
| 2006/0169290 | A1 | 8/2006 | Harris et al. |
| 2013/0167845 | A1 | 7/2013 | Grajek et al. |
| 2013/0167847 | A1 | 7/2013 | Rogers |
| 2013/0240402 | A1 | 9/2013 | Campista |
| 2015/0124941 | A1 | 5/2015 | Arterson |
| 2018/0214228 | A1 | 8/2018 | Toure et al. |

FOREIGN PATENT DOCUMENTS

| | | |
|---|---|---|
| DE | 19755763 C1 | 6/1999 |
| JP | 2000296123 A | 10/2000 |
| JP | 3120152 U | 3/2006 |
| KR | 2020150003432 U | 9/2015 |
| WO | 9717035 A1 | 5/1997 |

OTHER PUBLICATIONS

C-Arm Drape OEC® MiniView 6800 For OEC MiniView 6800 C-arm Systems 2, Mckesson Medical-Surgical Inc., Retrieved online from https://mms.mckesson.com/product/728160/Sterigear-10101 on Jan. 16, 2019, 2 pages.

International Patent Application No. PCT/US2020/028730, International Search Report and Written Opinion mailed Jul. 31, 2020, 12 pages.

* cited by examiner

STERILE DRAPE WITH ELASTICIZED BODY PORTION FOR PROTECTING A C-arm IMAGING MACHINE

RELATED MATTERS

This application is a continuation of U.S. patent application Ser. No. 16/851,760, filed Apr. 17, 2020, which claims the benefit of U.S. Provisional Patent Application No. 62/836,455, filed Apr. 19, 2019. The entire contents of each of these applications are incorporated herein by reference.

TECHNICAL FIELD

This disclosure relates to drapes used to provide a sterile barrier over medical equipment and, more particularly, to drapes for C-arm imaging machines.

BACKGROUND

A typical X-ray imaging system includes an X-ray source and an X-ray detector. X-rays emitted from the X-ray source can impinge on the X-ray detector and provide an X-ray image of an object or subject that is placed between the X-ray source and the detector. In different types of imaging systems, X-ray detectors are implemented using an image intensifier or a flat panel digital detector.

An imaging system may include an X-ray emitter and an X-ray detector positioned on opposite sides of an imaging arm or gantry assembly. For example, the emitter and detector may have a C-arm, G-arm, O-arm, L-arm, or other shaped arm. In either case, the arm assembly of the imaging system may move relative to the subject in order to acquire images from multiple angles. In some configurations, the arm can often be raised and lowered, be moved from side to side, and/or be rotated about one or more axes of rotation. Accordingly, the emitter and detector carried by the arm can be moved and reoriented to allow X-ray images to be taken from several different positions and angles and from one or more portions of a patient, without requiring the patient to be frequently repositioned.

An imaging system may be used during many different types of examinations and procedures with different patients. The components of the imaging system susceptible to contamination during a procedure, for example from patient contact or bodily fluid contact, may be wiped down and disinfected between patients. This can help minimize the possibility of cross-contamination and hospital acquired infection between procedures and patients. The facility housing the imaging system may clean the imaging system with a disinfecting agent between uses. To further enhance the sterility of the imaging environment, a disposable sterile drape may be placed over imaging system that is replaced between patients.

SUMMARY

In general, this disclosure is directed to a sterile drape for draping medical imaging equipment, such as a C-arm imaging system. The C-arm imaging system may include a detector that receives X-rays from an emitter positioned on an opposed side of the C-arm to generate an X-ray image of a subject that is placed between the emitter and detector. In some implementations, the detector is configured to rotate around an axis of rotation relative to the C-arm to orient the detector relative to the subject. In either case, the shape and maneuverability of the imaging system may make it difficult to adequately drape the surfaces of the imaging system and ensure that the surfaces remain draped during movement and use of the imaging system.

In some implementations according to the present disclosure a drape for covering a C-arm imaging machine is described. The drape includes a detector body cover, a C-arm body cover, and an elastic banding adjacent a junction between the detector body cover and the C-arm body cover. The detector body cover can be positioned over the detector of the imaging system to cover the detector from contamination. The C-arm body cover can define a tunnel extending away from the detector body cover. The C-arm body cover can cover a portion of the C-arm extending away from the detector. The elastic banding can provide a biasing force that compresses the drape against the C-arm adjacent the detector. For example, the elastic banding can extend about a perimeter between the detector body cover and the C-arm body cover to provide a biasing force encircling and/or enclosing the drape at that location. Configuring the drape with such an elastic banding can be useful, e.g., to facilitate positioning the detector body cover portion of the drape over different sized detectors on different imaging systems. Further, for imaging systems having a detector that is configured to rotate during use, the elastic banding can help keep the detector body cover retained around the detector even as the detector moves during operation.

While a drape according to the disclosure can have a variety of different configurations, in some examples, the drape includes a tail sheet extending away from the C-arm body cover. The tail sheet may be a section of drape material that does not surround the C-arm to the same extent as the tunnel portion of the C-arm body cover. For example, the C-arm body cover may define a tunnel configured to cover the C-arm on multiple sides whereas the tail sheet may be configured to cover the C-arm on fewer sides than that of the tunnel. In some implementations, the C-arm body cover forms a tunnel that extends from the detector body cover up to a joint about which the C-arm articulates. The tail sheet may cover a patient-facing surface of the C-arm extending beyond the joint.

In one example, a drape for a covering a C-arm imaging machine is described. The drape includes a detector body cover, a C-arm body cover, and an elastic banding. The detector body cover is configured to be positioned around a detector of the imaging machine. The C-arm body cover is configured to be positioned along at least a portion of a length of a C-arm of the imaging machine. The example specifies that the C-arm body cover defines a tunnel configured to surround the C-arm. The elastic banding extends about a perimeter of a junction between the detector body cover and the C-arm body cover and provides a biasing force configured to draw the junction between the detector body cover and the C-arm body cover closed.

In another example, a draped C-arm imaging machine is described. The draped machine includes a C-arm that is divided into a first side carrying a detector and a second side carrying an emitter, with the first side of the C-arm and the second side of the C-arm being divided by an articulating joint. The draped machine also includes a drape having a detector body cover, a C-arm body cover defining a tunnel, and an elastic banding extending about a perimeter of a junction between the detector body cover and the C-arm body cover. The example specifies that the drape covers at least a portion of the C-arm with the detector body cover positioned around the detector, the tunnel extending along at least a portion of a length of the first side of the C-arm from the detector body cover toward the articulating joint, and the elastic banding biasing the junction between the detector body cover and the C-arm body cover closed at a location between the detector and a reminder of the first side of the c-arm.

In another example, a method of draping a C-arm imaging machine is described. The method includes stretching an elastic banding joining a detector body cover to a C-arm body cover to enlarge an opening of the detector body cover thereby providing an enlarged opening to the detector body cover. The method includes positioning the detector body cover over a detector of a C-arm via the enlarged opening and allowing the elastic banding to contract around the C-arm. The method further includes positioning a tunnel of the C-arm body cover around at least a portion of the C-arm extending away from the detector.

The details of one or more examples are set forth in the accompanying drawings and the description below. Other features, objects, and advantages will be apparent from the description and drawings, and from the claims.

DETAILED DESCRIPTION

This disclosure is generally directed to a drape for an imaging machine, such as a C-arm x-ray imaging machine used during a fluoroscopy procedure. The drape can be deployed over a portion of the imaging machine to form a sterile barrier between the machine and the subject being imaged. In use, the drape may be received as a folded, flat-packed structure that is then unfolded and deployed over the imaging machine by a clinician. After an imaging procedure is performed on the subject, the drape may be removed from the imaging machine, discarded, and replaced with a fresh sterile drape.

While the following description focuses on a C-arm shaped imaging machine and a drape for such a C-arm imaging machine, it should be appreciated that a drape according to disclosure is not limited to such an example imaging machine. Rather, a drape according to disclosure can be configured for use on any type of imaging machine, including C-arms, G-arms, O-arms, L-arms, and other types of x-ray or non-x-ray imaging devices (e.g., microscopes). Accordingly, reference to certain aspects of a drape as being configured for a C-arm may be understood to be alternatively configured for a different shape when intended for a different machine configuration.

Details on example drapes according to disclosure are described with reference to FIGS. 3-6. Further, an example method of draping an imaging machine is described with reference to FIG. 7. However, details on example C-arm imaging machines that may be draped using a drape according to disclosure are first described with reference to FIGS. 1 and 2.

Figure 1:
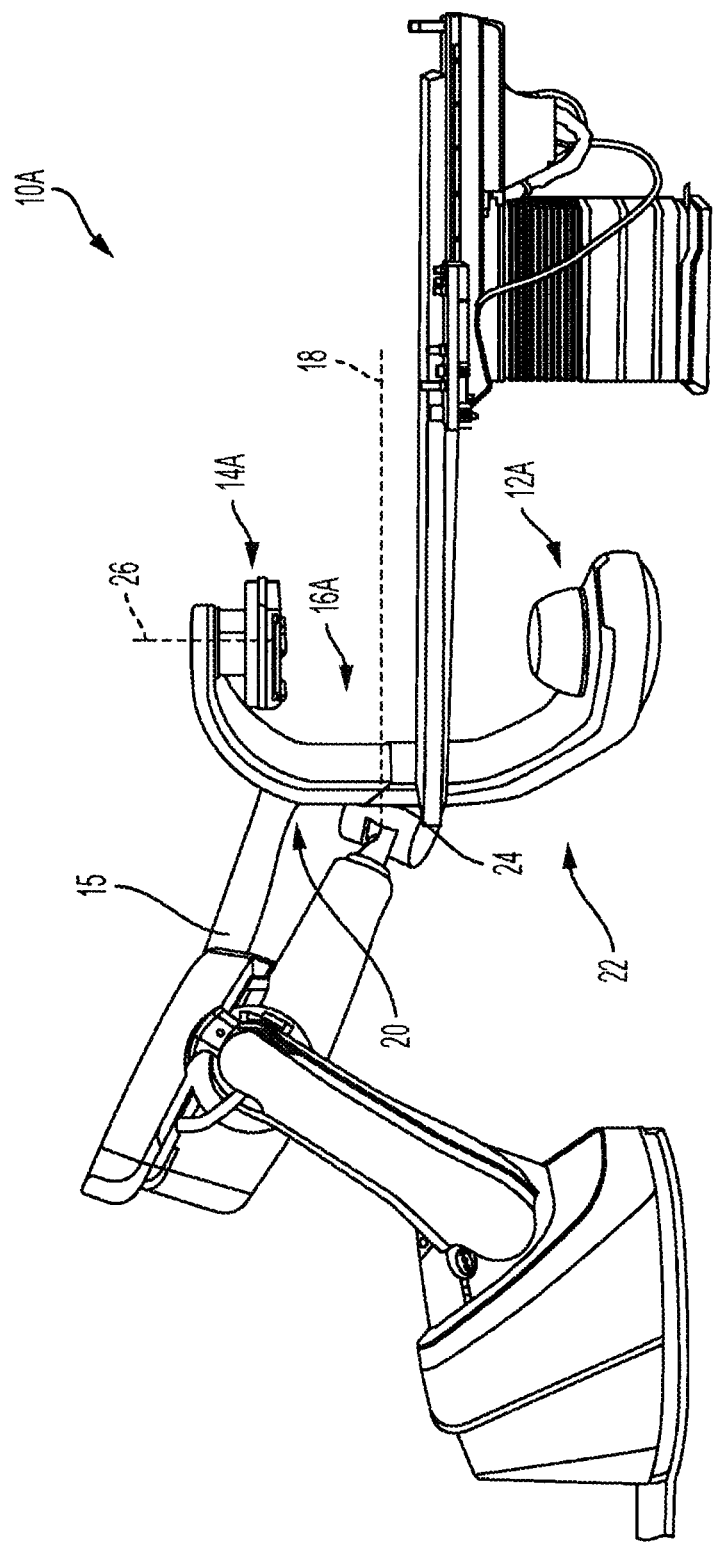
FIGS. 1 and 2 are perspective illustrations of two example C-arm imaging machines that may be protected with a drape according to the disclosure.
Figure 2:
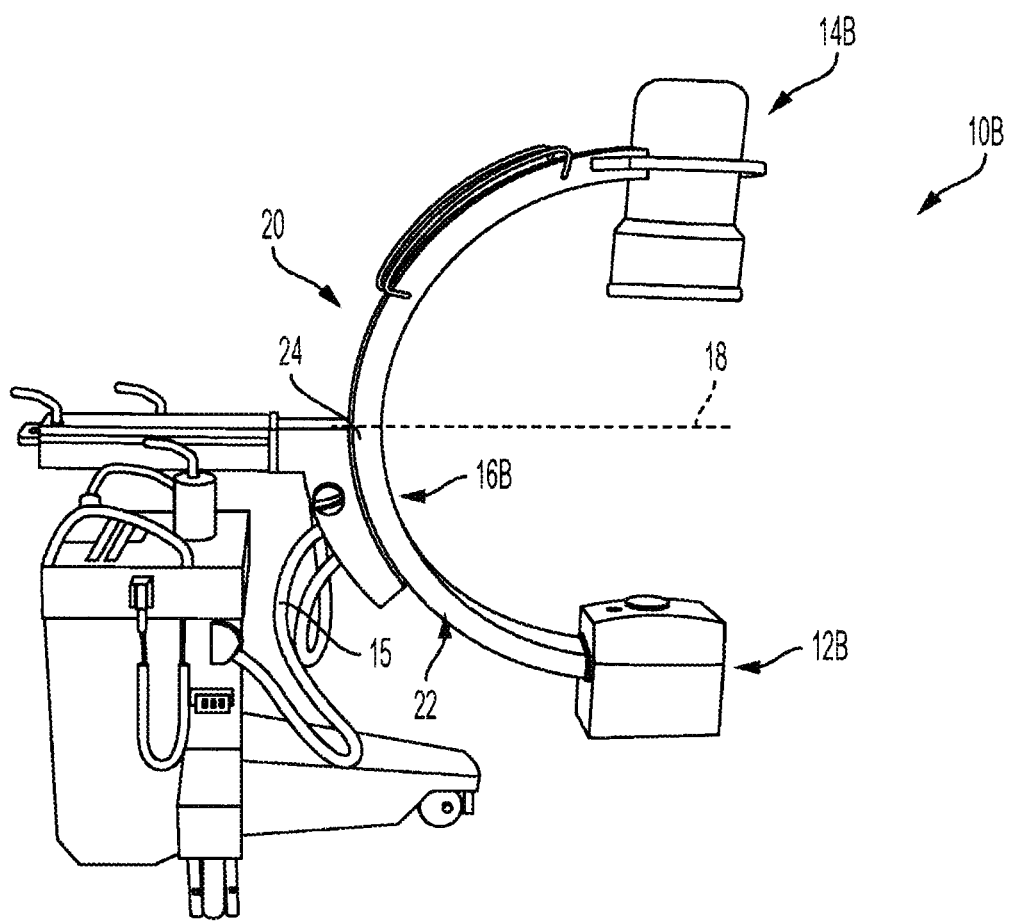

FIGS. 1 and 2 are perspective illustrations of two example C-arm imaging machines 10A and 10B (collectively referred to as "C-arm imaging machine 10" or "imaging machine 10"), which may be used to generate images of a subject as part of a medical diagnosis or procedure. Each C-arm imaging machine 10 includes an emitter 12A, 12B (collectively referred to as an "emitter 12"), which can generate and/or emit X-rays that are directed to penetrate the subject being imaged. Each C-arm imaging machine 10 also includes a detector 14A, 14B (collectively referred to as "detector 14"). Detector 14 can receive X-rays after having passed through the subject being imaged for generating a visible image of the portion of the subject imaged. Cabling 15 can supply power and/or signals to the emitter 12 and/or detector 14 and/or receive signals from one or both components.

In the example of FIG. 1, detector 14A on imaging machine 10A is illustrated in the form of a flat panel detector. A flat panel detector is typically formed of a semi-conductor material and is able to covert X-rays to visible light images. The flat panel detector may have a polygonal (e.g., square, rectangular) shape with a width and/or length greater than its thickness (where thickness is perpendicular to the subject being imaged). By contrast, detector 14B on imaging machine 10B of FIG. 2 is illustrated in the form of an image intensifier. An image intensifier may include a vacuum tube with an output phosphor coupled to a camera or a charge coupled device (CCD), to convert X-rays to visible light images. An image intensifier may have a thickness (in the direction perpendicular to the subject being imaged) greater than its length and/or width. In either case, a drape according to the disclosure can be configured to drape an imaging machine having any type of detector, including a flat panel detector or an imaging intensifier.

With further reference to FIGS. 1 and 2, C-arm imaging machine 10 is illustrated as having a C-arm 16A, 16B (collectively referred to as "C-arm 16"). C-arm 16 can define a generally C-shaped structure with emitter 12 positioned on one side of the arm and detector 14 positioned on an opposite side of the arm. The C-arm shape defined by C-arm 16 can allow emitter 12 and detector 14 to be simultaneously positioned on opposite sides of the patient being imaged during an imaging procedure.

While C-arm 16 is illustrated as having a general C-shape, and imaging detector arm that is draped in accordance with the present disclosure can have a variety of other shapes. For example, in other configurations, imaging machine 10 may have a G-arm, O-arm, L-arm, or other shaped arm.

C-arm 16 can be thought of as having two halves: one half carrying detector 14 and one half carry emitter 12. For example, C-arm 16 can be divided through a geometric center by a hypothetical axis 18 into a first side 20 carrying detector 14 and a second side 22 carrying emitter 12. The length of C-arm 16 can dictate the separation distance between emitter 12 and detector 14 and, correspondingly, the size of the subject matter that can be imaged using C-arm. For example, imaging machine 10 may be configured as a full-size imaging device (e.g., for imaging the body or torso of a patient) or a mini C-arm (e.g., for imaging an arm, a hand, a leg, a foot, or a smaller section of the body than the full torso).

In some configurations, C-arm 16 of imaging machine 10 can rotate or articulate about a joint 24. C-arm 16 may rotate about articulating joint 24 to allow different portions of the subject to be imaged without requiring the subject to be repositioned relative to the imaging device. In some configurations, C-arm 16 may advance forward and backward relative to articulating joint 24 in addition to or in lieu of rotating about the joint. This can allow emitter 12 and detector 14 to translate along a length of the subject in addition to or in lieu of rotating about the subject being imaged.

As briefly mentioned above, detector 14 of imaging machine 10 may be stationary or may rotate about an axis of rotation. In the example of FIG. 1, detector 14A is illustrated as a flat panel detector capable of rotating about an axis of rotation 26 (e.g., rotating from 90° to 360°. When so configured, detector 14 may rotate before and/or after applying a drape over the detector as discussed in more detail below.

As introduced above, a drape may be used to form a sterile barrier between imaging machine 10 and a patient (or other subject matter) being imaged. The drape can be positioned over at least a portion of imaging machine 10 before the patient undergoes imaging using the machine. After the imaging procedure, the drape can be removed from the machine and discarded in preparation a new patient.

Figure 3:
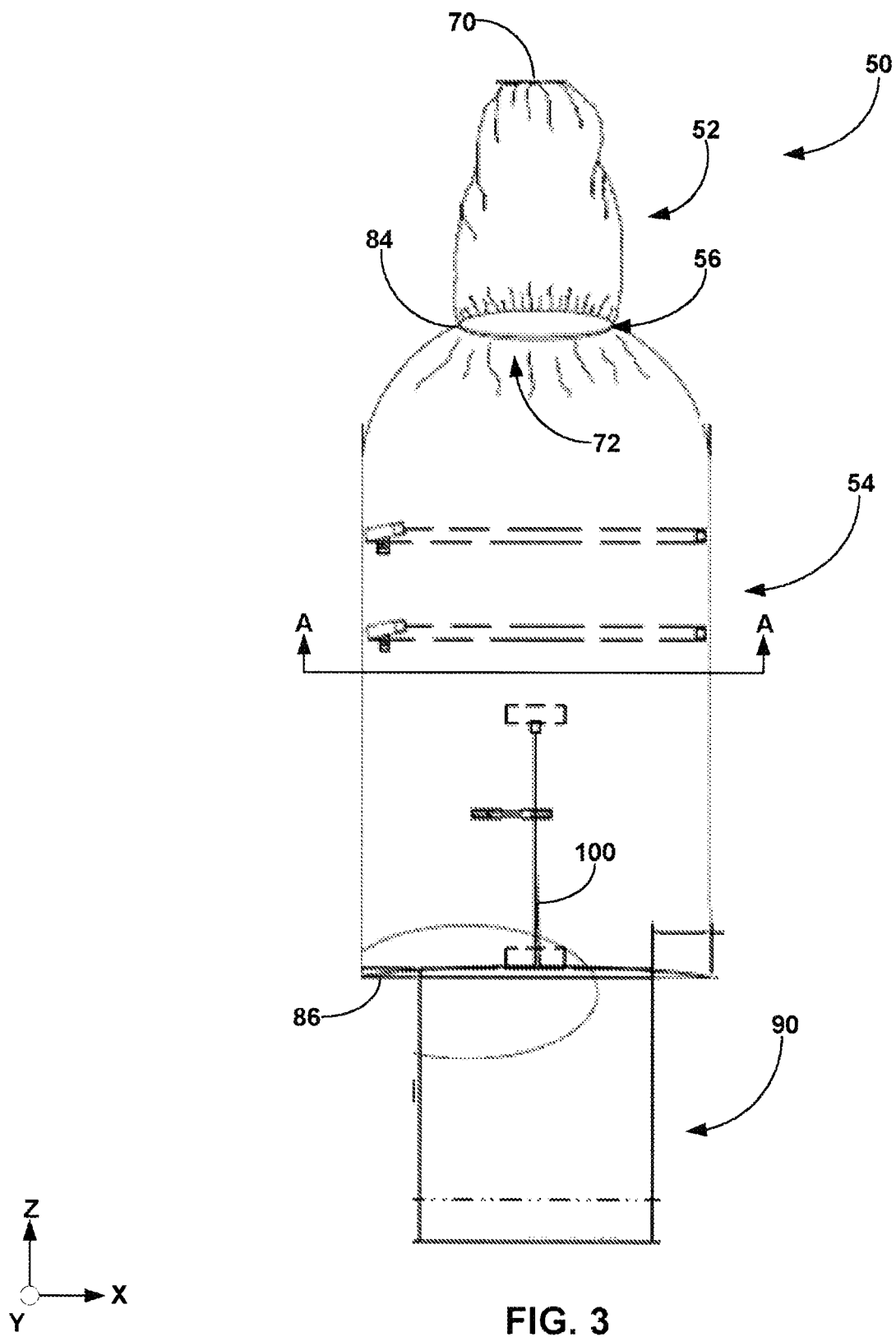
FIG. 3 is a top view illustration of an example drape that can be used to drape the example imaging machines of FIGS. 1 and 2.

FIG. 3 is a top view illustration of an example drape 50 that can be used to drape imaging machine 10 according to the disclosure. As shown in this example, drape 50 includes a detector body cover 52 and a C-arm body cover 54. Drape 50 is also illustrated as including an elastic banding 56. Detector body cover 52 can be configured to be positioned over detector 14 of imaging machine 10. C-arm body cover 54 may be joined to and extend away from detector body cover 52 for covering at least a portion of C-arm 16. Elastic banding may provide a biasing force helping to close drape 50 about C-arm 16 adjacent to detector 14.

In use, elastic banding 56 may be expanded and detector body cover 52 positioned over detector 14. Elastic banding 56 can then be allowed to contract to close detector body cover 52 around the detector, thereby enclosing the detector in the detector body cover. C-arm body cover 54 can then be pulled over a portion of C-arm 16 extending away from detector 14, e.g., toward emitter 12. Once deployed, drape 50 can help form a sterile barrier between imaging machine 10 and the subject being imaged.

In general, detector body cover 52 of drape 50 may be a section of drape material configured (e.g., size and shaped) to partially or completely surround detector 14 of imaging machine 10. In some implementations, detector body cover 52 may be shape indexed to the shape of detector 14 over which the detector body cover is intended to be positioned. In other implementations, detector body cover 52 may be a generic-shaped covering that is not shape indexed to the shape of detector 14. For example, detector body cover 52 may be a bag configured to be positioned over and completely surround imaging machine 10. When so configured, the bag of drape material defining detector body cover 52 may be positioned over the terminal end of C-arm 16 carrying detector 14 and pulled over the detector in a direction toward emitter 12 carried on opposed end of the C-arm body.

When drape 50 is intended to be deployed over an imaging machine 10 that has a detector 14 that rotates, detector body cover 52 may be sized large enough to allow detector 14 to rotate within the detector body cover. For example, detector body cover 52 may enclose an area as large or larger than the area swept out or otherwise traversed during rotation of detector 14 during full rotation of the detector. This can ensure that detector 14 can rotate to the maximum extent desired by the clinician and/or allowed by imaging machine 10 without drape 50 hindering rotation and/or the drape being ripped through rotation.

C-arm body cover 54 can be positioned along the length of C-arm 16 extending away from detector 14. After positioning detector body cover 52 over detector 14, C-arm body cover 54 can be pulled (e.g., stretched and/or extended) along the length of C-arm 16 in a direction toward emitter 12. In this way, C-arm body cover 54 can cover a portion of C-arm 16 adjacent to detector 14. In some configurations, C-arm body cover 54 may define a tunnel that is configured to surround the portion of C-arm over which the C-arm body cover is positioned.

Figure 4:
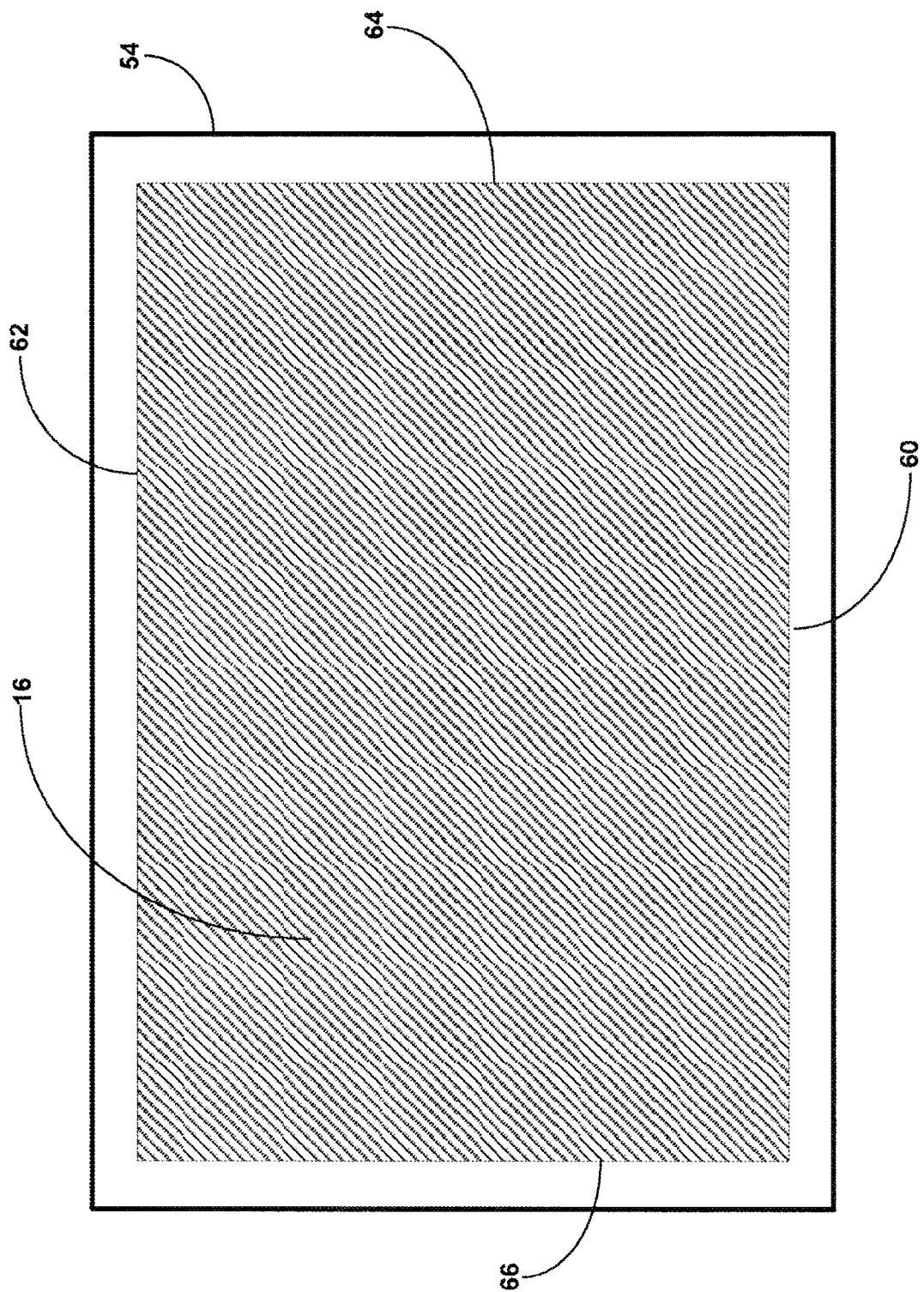
FIG. 4 is a sectional view of an example C-arm body cover portion of the drape of FIG. 3 taken along the A-A section line indicated on FIG. 3.

FIG. 4 is a sectional image of C-arm body cover 54 taken along the A-A section line indicated on FIG. 3 and illustrates an example configuration of C-arm body cover 54 surrounding C-arm 16. In this example sectional view, C-arm 16 defines a bottom surface 60, which may be a patient-facing surface when the C-arm is positioned relative to a patient undergoing an imaging procedure. C-arm 16 may also define a top surface 62 and one or more side surfaces 64, 66.

C-arm body cover 54 may define a tunnel surrounding C-arm 16. For example, as illustrated, C-arm body cover 54 may cover bottom surface 60 of the C-arm 16, top surface 62 of the C-arm body, and any side surfaces 64, 66 of the C-arm body. While the illustrated example shows C-arm 16 as having a rectangular cross-sectional shape and C-arm body cover 54 having a corresponding rectangular cross-sectional shape, it should be appreciated that C-arm 16 and/or C-arm body cover 54 may have any suitable cross-sectional shape. C-arm 16 and/or C-arm body cover 54 may define any polygonal (e.g., square, rectangle, triangle) or arcuate (e.g., circular, elliptical) shape, or even combinations of polygonal and arcuate shapes. Further, C-arm body cover 54 may have the same general cross-sectional shape as C-arm 16 or may have a different cross-sectional shape than the C-arm body. For instance, unlike the example of FIG. 4 where C-arm 16 and C-arm body cover 54 have the same cross-sectional shape, C-arm 16 may have a generally rectangular cross-sectional shape whereas C-arm body cover 54 may have a generally circular cross-sectional shape.

In some implementations, detector body cover 52 and C-arm body cover 54 are separate sections of draping (each of which may be formed of one or more pieces of draping material) that are joined together to form a unitary drape 50. In other implementations, detector body cover 52 and C-arm body cover 54 may be formed of a single sheet of drape material rather than separate sections of drape material joined together. In either case, elastic banding 56 may define a junction that separates the portion of drape 50 referred to as detector body cover 52 from the portion of the drape referred to its C-arm body cover 54.

In general, elastic banding 56 may be formed of a material that can be deformed from its original shape (e.g., through stretching or other enlarging) and elastically return to its original shape and/or length. For example, elastic banding 56 may be formed of a polymeric material, such as rubber, that can be stretched to an enlarged size and which then provides a biasing or compression force drawing the elastic banding back down to its non-stretch size. Elastic banding 56 may be formed solely of elastic material or may be integrated with another material, such as woven, braided, or knitted elastic that may include strips of rubber integrated with a fabric material.

Elastic banding 56 can extend partially or fully about a perimeter of drape 50, e.g., at the junction between detector body cover 52 and C-arm body cover 54. Elastic banding 56 can be a single continuous section (e.g., strip) of material extending about the perimeter or can be multiple sections (e.g., strips) of material positioned at different locations about the perimeter. In this latter implementation, the multiple sections of elastic banding material may be joined together to form a composite continuous strip or may be separated from each other to form a discontinuous elastic banding about the perimeter.

As one example, detector body cover 52 may define a bag configured to completely surround detector 14 of imaging machine 10. The bag may have a closed terminal end 70 and define an opening 72 at the junction with C-arm body cover 54. A pathway may be formed from the tunnel defined by C-arm body cover 54 into the bag forming detector body cover 52. Accordingly, C-arm 16 can extend through the tunnel defined by C-arm body cover 54 with the terminal end of the C-arm body carrying detector 14 inserted into the open end 72 of detector body cover 52, thereby covering detector 14 with detector body cover 52.

Elastic banding 56 can extend about a perimeter (e.g., circumference) of drape 50. The unexpanded size of elastic banding 56 may be smaller than or approximately equal to a cross-sectional size of C-arm 16. As a result, elastic banding 56 may draw drape 50 closed against C-arm 16 at the location of the C-arm body over which elastic banding 56 is positioned. In this way, elastic banding 56 can help secure drape 50 to imaging machine 10 and, more particularly, help close open end 72 of detector body cover 52 around detector 14 of the imaging machine.

The location of drape 50 where elastic banding 56 is positioned can define the junction between detector body cover 52 and C-arm body cover 54. As a result, the section of drape 50 distal of elastic banding 56 (e.g., encompassing closed end 70) may be designated as detector body cover 52 whereas the section of the drape proximal the elastic banding may be designated as C-arm body cover 54. In implementations where detector body cover 52 and C-arm body cover 54 are formed of separate sheets of material joined together, the physical interface or meeting location between the separate sheets of material may or may not overlap with elastic banding 56.

Elastic banding 56 can be joined to drape 50 using a variety of different fixation techniques. As one example, elastic banding 56 can be adhesively attached to drape 50. As another example, elastic bending 56 can be thermally attached to drape 50, e.g., by applying heat to the drape to temporarily melt the portion of the drape and thereby bond elastic banding to the melted portion of drape. As still another example, elastic banding 56 can be attached to drape 50 using one or more mechanical fixation elements, such as pins, snaps, hook and loop fasteners, and/or stitching. Independent of the type of attention element used to secure elastic bending 56 to drape 50, the elastic banding may be attached to an interior surface of the drape, and exterior surface of the drape, and/or between two sections of drape material (e.g., as an interstitial material bridging two sections of draping).

In some implementations, elastic banding 56 is incorporated into drape 50 using stitching. Stitching may provide a robust physical connection between elastic banding and one or more layers of drape material, helping to ensure that elastic banding 56 remains tightly secured to the drape material during stretching and compression. When so implemented, elastic banding 56 can be sewn to one or more sheets of drape material forming detector body cover 52 and/or C-arm body cover 54.

Figure 5:
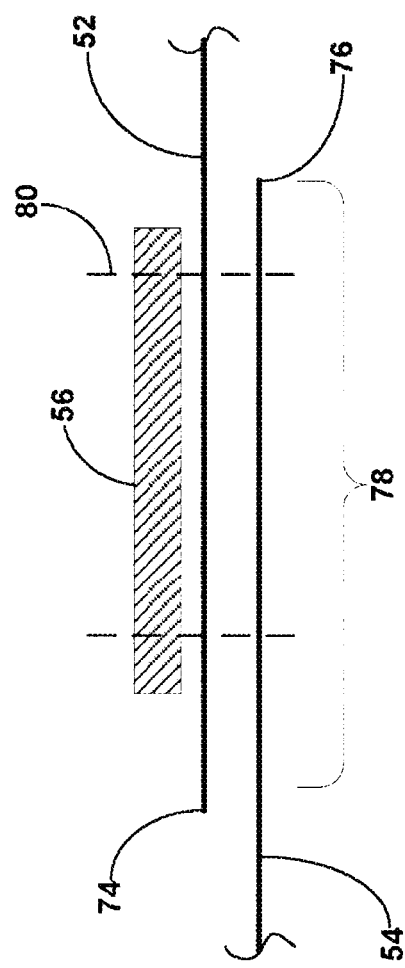
FIG. 5 is a side view of an example drape material arrangement that may be used to fixate elastic banding in the drape of FIG. 3.

FIG. 5 is a side view of an example drape material arrangement that may be used to fixate elastic banding 56 to drape 50. As shown in this example, one or more sections of drape material forming detector body cover 52 terminate in first terminal edge 74 (e.g., defining open end 72). Further, one or more sections of drape material forming C-arm body cover 54 terminate in a second terminal edge 76. The first terminal edge 74 of detector body cover 52 is overlapped with the second terminal edge 76 of C-arm body cover 54 to define an overlap region 78. Elastic banding 56 is attached overlaying overlap region 78, e.g., to provide an interlocking sandwiched section of materials. Elastic banding 56 can be attached using any suitable attachment technique, including those discussed above. In some examples, however, elastic banding is attached using stitching 80. For example, elastic banding may be attached using an over lock stitching technique, which may also referred to as a serge stitching technique, to secure elastic banding in different sections of drape material forming detector body cover 52 and C-arm body cover 54, respectively.

It should be appreciated that although FIG. 5 illustrates detector body cover 52 positioned on top of C-arm body cover 54, and elastic banding 56 on top of detector body cover 52, an alternative arrangement of layers can be used without departing from the scope of the disclosure. For example, C-arm body cover 54 may be positioned on top of detector body cover 52, with elastic banding 56 further positioned on top of the C-arm body cover. As another example, elastic bending 56 may be positioned between detector body cover 52 and C-arm body cover 54.

With further reference to FIG. 3, C-arm body cover 54 is illustrated as extending from a first end 84 to a second end 86. The first end 84 of C-arm body cover 54 may be the junction with detector body cover 52 where elastic banding 56 is located. The second end 86 of C-arm body cover 54 may be the location where the proximal-most end of the tunnel defined by the C-arm body cover terminates.

In some examples, including the example illustrated in FIG. 3, drape 50 includes a further section of drape material 90 extending proximally from the second or terminal end 86 of C-arm body cover 54. In other examples, drape 50 does not include this further section of drape material 90. When drape 50 includes a further section of drape material 90 extending beyond the end of the tunnel defined by C-arm body cover 54, the additional section of drape material may be referred to as a tail sheet. Tail sheet 90 of drape 50 can extend outwardly from the second and 86 of the tunnel formed by C-arm body cover 54, providing additional draping that can be attached to imaging machine 10.

When configured with a tail sheet 90, the tail sheet may be positionable against the portion of C-arm 16 located beyond the section of the C-arm covered by the tunnel of C-arm body cover 54 (e.g., proximately along the length of the C-arm). With reference to imaging machine 10 in FIG. 1, for example, the tunnel portion of C-arm body cover 54 may extend from detector 14 (which is covered by detector body cover 52) down along the length of C-arm 16 toward emitter 12. The tunnel portion of C-arm body cover 54 may extend from the detector 14 down to a location adjacent joint 24 of imaging machine 10, e.g., location distal of or just short of joint 24. The presence of joint 24 may prevent the tunnel from continuing to pass over the joint and down along C-arm 16, e.g., because the joint may interfere with the top surface of sheet material defining the tunnel. For this reason, the tunnel portion of C-arm body cover 54 may have a size effective to extend between detector 14 and joint 24 but not beyond the joint. As a result, the first half 20 of C-arm 16 may generally be covered by drape 50 (e.g., detector body cover 52 and the tunnel portion of C-arm body cover 54). Tail sheet 90 may provide a section of drape material that can extend beyond joint 24 and down over at least a portion of second half 22 of C-arm 16, e.g., beyond the joint.

For example, tail sheet 90 may be formed of a planar sheet of drape material (optionally with sidewalls) that does not have a top surface that can interfere with joint 24. As a result, tail sheet 90 can continue extending down along the length of C-arm 16 beyond joint 24. Tail sheet 90 may not cover all sides of C-arm 16 but may instead be positioned covering the patient-facing surface 60 of the C-arm. In applications where second-half 22 of C-arm 16 is less likely to become contaminated than the first half 20 of the C-arm, this more limited draping provided by tail sheet 90 can still provide appropriate sterility protection for the C-arm. Tail sheet 90 may optionally have sidewalls that cover the side surfaces of C-arm 16 in addition to covering patient-facing surface 60. The sidewalls may even wrap (e.g., partially) around top surface 62 of C-arm 16 or, in other implementations, may not cover any of top surface 62 of the C-arm.

In examples where drape 50 does not include tail sheet 90, the tunnel portion of C-arm body cover 54 may or may not be alternatively configured to extend past joint 24 to cover a portion of the second half 22 of C-arm 16. If the tunnel portion of C-arm body cover 54 is intended to extend past joint 24 of imaging machine 10, a slit or other opening may be provided in the top surface of the tunnel to allow the tunnel to be drawn over and/or passed by joint 24.

Figure 6:
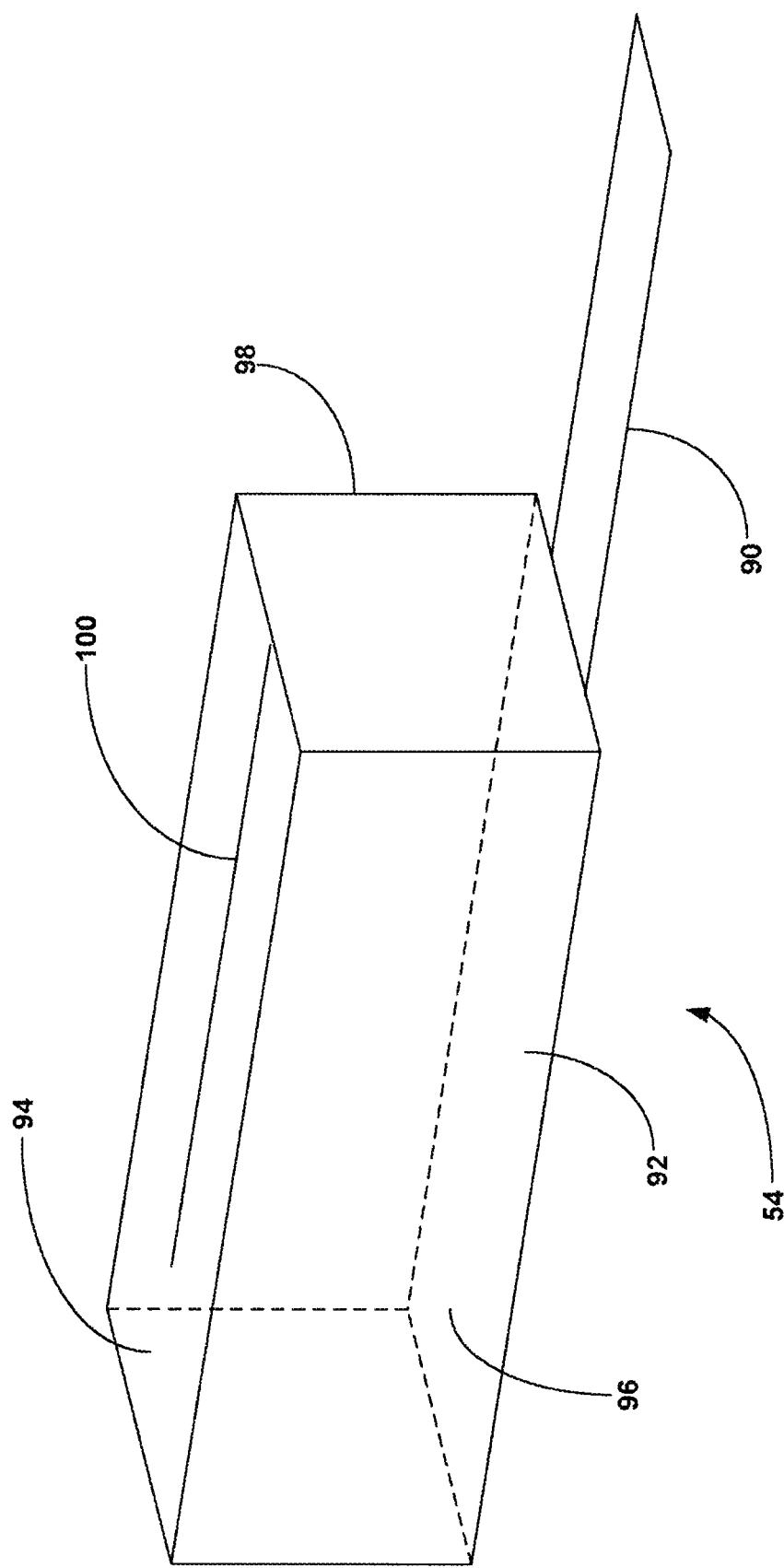
FIG. 6 is a perspective view of an example arrangement of a tunnel portion relative to a tail sheet of the C-arm body cover of FIG. 3.

When C-arm body cover 54 of drape 50 includes tail sheet 90, the tail sheet may extend from a bottom or patient-facing side of the tunnel portion of C-arm body cover 54. For example, FIG. 6 is a perspective view of an example arrangement of the tunnel portion of C-arm body cover 54 relative to tail sheet 90. As shown in this example, tail sheet 90 extends from the second end 86 of the tunnel. In particular, in the illustrated arrangement, the tunnel portion of C-arm body cover 54 defines a bottom wall 92 configured to cover the patient-facing surface 60 of the C-arm 16, a top wall 94 configured to cover an outward facing surface of the C-arm 16 (e.g., surface opposite the patient-facing surface), a first sidewall 96 joining the top wall to the bottom wall, and a second sidewall 98 joining the top wall to the bottom wall.

Tail sheet 90 can extend from the bottom wall 92 of the tunnel, e.g., and be integral with or joined to the bottom wall. Accordingly, tail sheet 90 can also cover the patient-facing surface 60 of C-arm 16, e.g., over a length of the C-arm located beyond the terminal end 86 of the tunnel. For example, the tunnel portion of C-arm body cover 54 may have a length that extends from the junction of detector body cover 52 to joint 24 of imaging machine 10. Tail sheet 90 may have a length that allows the tail sheet to be positioned covering patient-facing surface 60 overlying joint 24 and beyond, toward emitter 12. Tail sheet 90 may extend over joint 24 by covering the patient-facing surface 60 of C-arm 16 that is on the opposite side of joint 24.

Tail sheet 90 may have a length that extends past joint 24 of imaging machine 10 down toward emitter 12. Tail sheet 90 may extend down to emitter 12 or a distance along C-arm 16 short of emitter 12. A separate banded bag drape may be positioned over emitter 12 (optionally covering the terminal end of tail sheet 90) to provide a sterile barrier over the emitter. In another configuration, drape 50 may include an emitter body cover extending from the terminal end of tail sheet 90 that can be positioned over emitter 12. The emitter body cover may be a bag having an open and in a closed end, similar to an example configuration of detector body cover 52 described above. When so configured, the emitter body cover may or may not also include a separate elastic banding to close the cover around emitter 12, e.g., configured consistent with elastic banding 56 described above.

In some configurations in which C-arm body cover 54 is configured with a tunnel section, the tunnel suction section may include a seam extending along at least a portion of the length of the tunnel to help facilitate installation of the tunnel about C-arm 16. For example, in FIG. 3, the tunnel portion of C-arm body cover 54 is illustrated as including a seam 100. Seam 100 may be a slit that allows the tunnel to split open for positioning around C-arm 16 and that can be close back together once the tunnel is positioned around the C-arm.

In different examples, seam 100 may extend the entire length of the tunnel or less than the entire length of the tunnel. For example, seam 100 may extend from second terminal end 86 toward first terminal end 84 but may stop short of the first terminal end, as shown in the illustrated example. Seam 100 may be formed in top surface 94 of the tunnel section of C-arm body cover 54 (FIG. 6) to prevent any breaks in the sterility barrier provided by patient-facing surface 92 of the tunnel section. Alternatively, seam 100 may be formed in a different surface of the tunnel portion of C-arm body cover 54, such as a sidewall surface or even the patient-facing surface.

When tunnel portion of C-arm body cover 54 is configured with seam 100, one or more closure elements may be positioned along the length of the seam to help secure the seam closed, when the tunnel is positioned over C-arm 16. Example closure elements that may be used include snaps, buttons, hook and loop fasteners, adhesive strips, and the like. After the split sides of the tunnel are drawn back together to close seam 100, the one or more closure elements can be engaged to keep the sides of the tunnel together and help close seam 100.

In general, drape 50, including detector body cover 52 and C-arm body cover 54, can be made of a sterile (and/or sterilizable) material that can be disposed of after a single use. Drape 50 may be typically fabricated from one or more types of polymeric material, such as polyethylene, polypropylene, polystyrene, or yet other types of drape material. After manufacture but before use, drape 50 may or may not be sterilized to ensure that the drape provides a sterile barrier between patient and imaging machine 10. For example, drape 50 may be subject to a sterilization process, such as steam sterilization, dry heat sterilization, ethylene oxide gas sterilization, or radiation sterilization.

In some implementations, drape 50 can include additional features to help attach and secure the drape to imaging machine 10 during use. For example, drape 50 can include one or more sections of pressure sensitive adhesive disposed on a surface of the drape that can be pressed against a corresponding section of imaging machine 10 over which the drape is intended to provide protection. For example, when drape 50 includes tail sheet 90, the outward facing surface of the tail section that is intended to contact C-arm 16 can include one or more sections of pressure sensitive adhesive. The one or more sections of pressure sensitive adhesive can be covered by release liner or otherwise protected to prevent the pressure sensitive adhesive from inadvertently bonding one section of drape to another while the drape is folded. In either case, the one or more sections of pressure sensitive adhesive can be exposed for contact during unfolding and/or deployment of drape 50. As drape 50 is positioned over imaging machine 10, the one or more sections of pressure sensitive adhesive carried by the drape can be pressed against the machine to help secure and hold the drape to machine. Other types of attachment features that can be incorporated into drape 50 and used to secure a portion of the drape to imaging machine 10 (e.g., detector 14 and/or C-arm 16) in addition to or in lieu of pressure sensitive adhesive include ties, magnetic connectors, and the like.

Drape 50 can have a variety of different sizes, and the specific size of drape 50 and its components may vary depending on the size of imaging machine intended to be covered by the drape. In some examples, detector body cover 52 of drape 50 has a length (in the Z-direction indicated on FIG. 3) less than the length of C-arm body cover 54 (e.g., the tunnel portion of the C-arm body cover) and/or a width (in the X-direction indicated on FIG. 3) less than the width of C-arm body cover 54 (e.g., the tunnel portion of the C-arm body cover). When configured with tail sheet 90, the tail sheet, in some examples, may have a length less than the length of the tunnel portion of the C-arm body cover and/or a width less than the width of the tunnel portion of the C-arm body cover.

Figure 7:
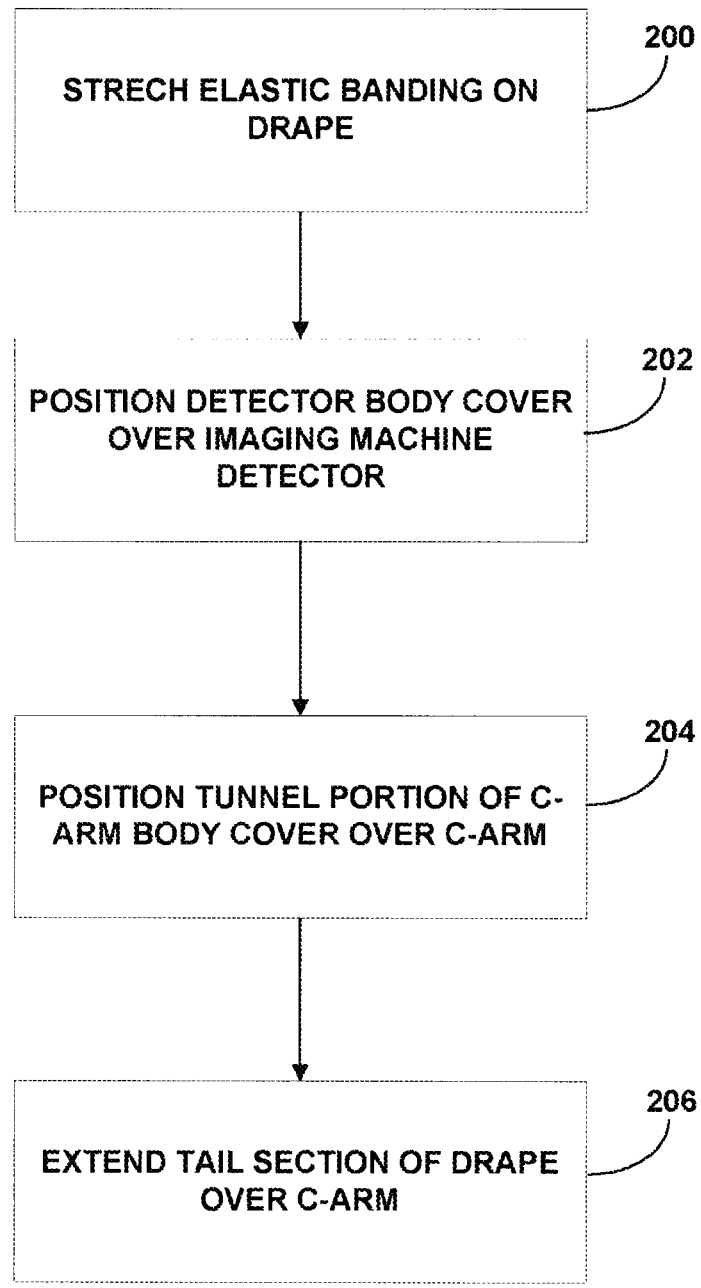
FIG. 7 is a flow diagram illustrating an example technique for draping an imaging machine using a drape according to disclosure.

FIG. 7 is a flow diagram illustrating an example technique for draping an imaging machine using a drape according to disclosure. The technique of FIG. 7 will be described with respect to imaging machine 10 and drape 50 although can be performed using other configurations of medical devices and drapes, as described herein.

The example technique of FIG. 7 includes stretching elastic banding 56 joining detector body cover 52 to C-arm body cover 54 to enlarge open end 72 of the detector body cover. (200) This can provide an enlarged detector body cover opening for positioning the detector body cover 52 over detector 14. For example, once elastic banding 56 is stretched to enlarge the opening of detector body cover 52, the detector body cover can be positioned over detector 14. (202) In some applications, the user stretches elastic banding 56 to enlarge the open end 72 of detector body cover 52 before slipping the detector body cover over detector 14. In other applications, the user may stretch elastic banding 56 concurrent with positioning the detector body cover 52 over detector 14. For instance, in the process of pulling detector body cover 52 over detector 14, the larger size of detector 14 relative to the necked down region of drape 50 provided by elastic banding 56 may cause the elastic banding to stretch as the detector body cover is slipped over the end of the C-arm to cover detector 14.

In either case, elastic banding 56 can compress towards its natural, unbiased size, causing the elastic banding to compress drape 50 around C-arm 16. This can result in drape 50 having a narrower circumference in the region of elastic banding 56 compressing against C-arm 16 than either immediately proximal or distal of the elastic banding.

The technique of FIG. 7 also includes positioning the tunnel portion defined by C-arm body cover 54 around the portion of C-arm 16 extending away from detector 14. (204). For example, with detector body cover 52 positioned over detector 14 and elastic banding 56 drawing detector body cover 52 closed around C-arm 16, the tunnel portion can be drawn down the C-arm towards emitter 12. In some implementations where drape 50 includes seam 100, the user may split the tunnel portion of C-arm body cover 54 apart using the seam to facilitate installation of the tunnel over C-arm 16. The user can pull each side of the tunnel portion of C-arm body cover 54 toward emitter 12 and draw the two sides together to close seam 100. One or more fasteners may be used to secure seam 100 closed, e.g., over the outward facing surface of C-arm 16. In some configurations, the user pulls the tunnel portion of C-arm body cover 54 down C-arm 16 from a location adjacent detector 14 to a terminal location adjacent joint 24.

The example technique of FIG. 7 also includes extending tail sheet 90 over a portion of C-arm 16 extending beyond the terminal end of the tunnel portion of C-arm body cover 54. (206) For example, the tunnel portion of C-arm body cover 54 may terminate adjacent joint 24 (although may terminate at other locations in other configurations). Tail sheet 90 can be extended along the patient-facing surface of C-arm 16 toward emitter 12 beyond where the tunnel portion of C-arm body cover 54 terminates. Tail sheet 90 may include one or more sections of pressure sensitive adhesive or other fixation features, allowing the user to secure tail sheet 90 to C-arm 16. For example, tail sheet 90 may include one or more sections of pressure sensitive adhesive, and a user may press tail sheet 90 against the patient-facing surface of C-arm 16 to adhere the tail section to the C-arm.

Figure 8:
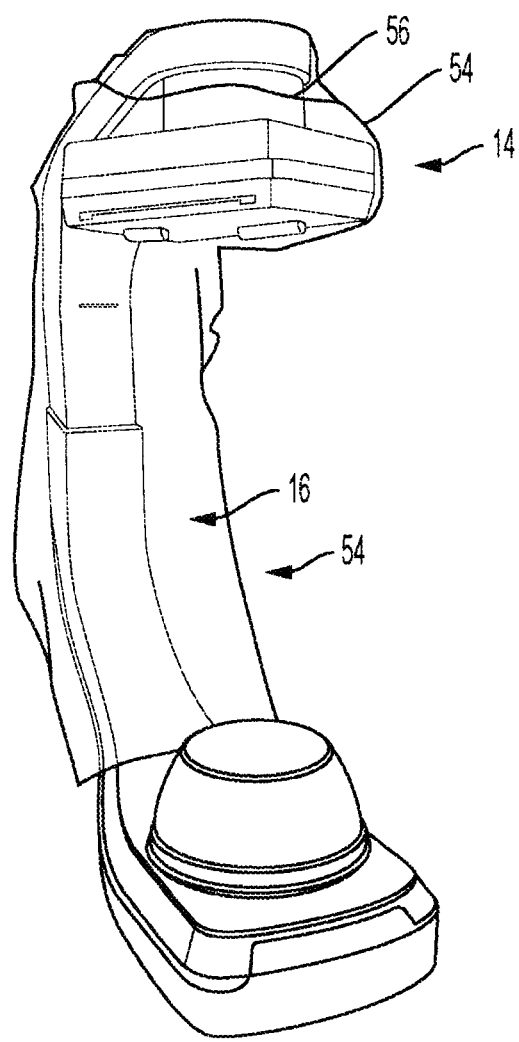
FIGS. 8 and 9 are illustrations of an example C-arm imaging machine draped with an example drape according to the disclosure.
Figure 9:
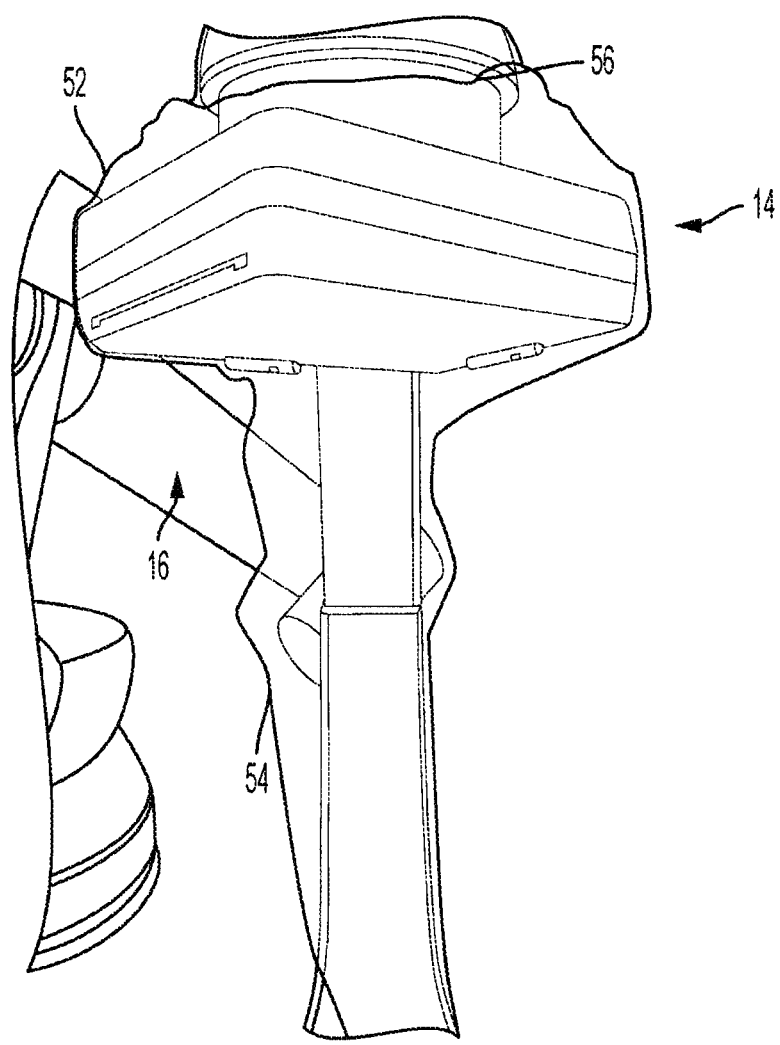

FIGS. 8 and 9 are illustrations of an example C-arm imaging machine draped with an example drape according to the disclosure.

A drape according to the disclosure can provide a barrier that protects a variety of different configurations of medical devices, including imaging machines. The drape can be easily and conveniently deployed over an imaging machine and secured to the machine to prevent unintended dislodgment during use. The drape can provide a comprehensive barrier, helping to prevent contaminants from one patient from contacting the image machine and cross contaminating for a subsequent patient.

Various examples have been described. These and other examples are within the scope of the following claims.

The invention claimed is:

1. A drape for a covering a C-arm imaging machine, the drape comprising:
   a detector body cover configured to be positioned around a detector of an imaging machine;
   a C-arm body cover configured to be positioned along at least a portion of a length of a C-arm of the imaging machine, the C-arm body cover defining a tunnel configured to surround the C-arm;
   an elastic banding extending about a perimeter of a junction between the detector body cover and the C-arm body cover, the elastic banding providing a biasing force configured to draw the junction between the detector body cover and the C-arm body cover closed.

2. The drape of claim 1, wherein
   the detector body cover defines a first terminal edge,
   the C-arm body cover defines a second terminal edge,
   the first terminal edge of the detector body cover is overlapped with the second terminal edge of the C-arm body to define an overlap region, and
   the elastic banding is attached overlaying the overlap region.

3. The drape of claim 1, wherein the elastic banding is a continuous length of elastic material extending around an entirety of the perimeter.

4. The drape of claim 1, wherein
   the detector body cover defines a bag configured to completely surround the detector, the bag defines an opening at the junction with the C-arm body cover, and the opening of the bag forms a pathway with the tunnel of the C-arm body through which the C-arm is configured to extend to connect to the detector body.

5. The drape of claim 1, wherein the tunnel is configured to surround the C-arm by covering a bottom surface of the C-arm, a top surface of the C-arm, and any side surfaces of the C-arm.

6. The drape of claim 1, wherein the tunnel extends from a first end at the junction to a second end configured to be positioned down the length of the C-arm.

7. The drape of claim 6, wherein the tunnel defines a bottom wall configured to cover the patient-facing surface of the C-arm, a top wall configured to cover an outward-facing surface of the C-arm, a first sidewall joining the top wall to the bottom wall, and a second sidewall joining the top wall to the bottom wall.

8. The drape of claim 1, wherein the elastic banding is attached via stitching to the detector body cover and the C-arm body cover.

9. The drape of claim 1, wherein the C-arm is divided into a first side carrying the detector and a second side carrying an emitter, the first side of the C-arm and the second side of the C-arm being divided by an articulating joint.

10. A draped C-arm imaging machine comprising:
a C-arm that is divided into a first side carrying a detector and a second side carrying an emitter, the first side of the C-arm and the second side of the C-arm being divided by an articulating joint; and
a drape comprising a detector body cover, a C-arm body cover defining a tunnel, and an elastic banding extending about a perimeter of a junction between the detector body cover and the C-arm body cover,
wherein the drape covers at least a portion of the C-arm with the detector body cover positioned around the detector, the tunnel extending along at least a portion of a length of the first side of the C-arm from the detector body cover toward the articulating joint, and the elastic banding biasing the junction between the detector body cover and the C-arm body cover closed at a location between the detector and a reminder of the first side of the c-arm.

11. The draped C-arm imaging machine of claim 10, wherein:
the detector body cover defines a first terminal edge,
the C-arm body cover defines a second terminal edge,
the first terminal edge of the detector body cover is overlapped with the second terminal edge of the C-arm body to define an overlap region, and
the elastic banding is attached via stitching overlaying the overlap region.

12. The draped C-arm imaging machine of claim 10, wherein the tunnel defines a bottom wall covering a patient-facing surface of the C-arm, a top wall covering an outward-facing surface of the C-arm, a first sidewall joining the top wall to the bottom wall, and a second sidewall joining the top wall to the bottom wall.

13. A method of draping a C-arm imaging machine comprising:
stretching an elastic banding joining a detector body cover to a C-arm body cover to enlarge an opening of the detector body cover thereby providing an enlarged opening to the detector body cover;
positioning the detector body cover over a detector of a C-arm via the enlarged opening and allowing the elastic banding to contract around the C-arm;
positioning a tunnel of the C-arm body cover around at least a portion of the C-arm extending away from the detector.

14. The method of claim 13, wherein positioning the tunnel of the C-arm body cover around at least a portion of the C-arm comprises surrounding the portion of the C-arm with the tunnel by covering a bottom surface of the C-arm, a top surface of the C-arm, and any side surfaces of the C-arm over the portion covered by the tunnel.

15. The method of claim 13, wherein positioning the tunnel of the C-arm body cover around at least a portion of the C-arm extending away from the detector comprises positioning the tunnel of the C-arm body cover from the detector toward but short of an articulating joint dividing the C-arm into a first side carrying the detector and a second side carrying an emitter.

16. The method of claim 13, wherein the tunnel defines a bottom wall, a top wall, and a first sidewall joining the top wall to the bottom wall, and a second sidewall joining the top wall to the bottom wall, and positioning the tunnel of the C-arm body cover around at least a portion of the C-arm comprises covering a patient-facing surface of the C-arm with the bottom wall, covering an outward-facing surface of the C-arm with the top wall, and covering sidewalls of the C-arm with the first sidewall the second sidewall.

* * * * *